United States Patent [19]
King et al.

[11] Patent Number: 5,939,642
[45] Date of Patent: Aug. 17, 1999

[54] GYRATORY COMPACTOR

[75] Inventors: Michael L. King, Durham; John T. Eagan, Jr., Cary; Donald K. McAlister, Apex, all of N.C.

[73] Assignee: Troxler Electronic Laboratories, Inc., Research Triangle Park, N.C.

[21] Appl. No.: 09/048,247

[22] Filed: Mar. 25, 1998

[51] Int. Cl.⁶ .................................................. G01N 3/32
[52] U.S. Cl. ............................................................ 73/813
[58] Field of Search .................................. 73/865.6, 866, 73/813, 818, 808, 803, 804, 841, 794, 795

[56] References Cited

U.S. PATENT DOCUMENTS

| | | |
|---|---|---|
| 2,972,249 | 2/1961 | McRae et al. ............................ 73/818 |
| 2,980,978 | 4/1961 | Marshall . |
| 3,374,665 | 3/1968 | Preston . |
| 3,478,572 | 11/1969 | McRae et al. . |
| 3,781,156 | 12/1973 | Moore . |
| 3,883,278 | 5/1975 | Hass . |
| 3,907,474 | 9/1975 | Blaser et al. . |
| 4,063,859 | 12/1977 | Halle et al. . |
| 4,140,744 | 2/1979 | Karas et al. . |
| 4,196,635 | 4/1980 | Zuber et al. . |
| 4,942,768 | 7/1990 | McRae . |
| 5,036,709 | 8/1991 | McRae ...................................... 73/841 |
| 5,046,367 | 9/1991 | Iizuka . |
| 5,275,056 | 1/1994 | Hamilton et al. ......................... 73/794 |
| 5,323,655 | 6/1994 | Eagan et al. ................................ 73/84 |
| 5,456,118 | 10/1995 | Hines et al. . |
| 5,606,133 | 2/1997 | Hines et al. . |

FOREIGN PATENT DOCUMENTS

| | | |
|---|---|---|
| 61-102536 | 5/1986 | Japan . |
| 1-118742 | 5/1989 | Japan . |

OTHER PUBLICATIONS

Pine Instrument Company Brochure, Model AFGC125X Gyratory Compactor.
Pine Instrument Company Brochure, Portable Gyratory Compactor AFG1.
Industrial Process Controls Ltd. Technical Brief, Servopac–Gyratory Shear Compactor.
Interlaken Technology Corporation Brochure, ITC Gyratory Compactor.
Instron Corporation Brochure, Gyratory Compactor.
Test Quip, Inc. Brochure, Brovold Gyratory Compactor.
Rainhart Co. Catalog No. 654, p. 6, Apr. 1965.
Rainhart Series 650 Sample Extruder, Rainhart Co. Catalog No. 650, May 1968.
Forneys Catalog, p. 117, 1983.
Marui Catalog, p. 65, 1988.
Huber, Gerald A. et al., "Development of the Superpave Gyratory Compactor", The Superpave Center, The University of Texas at Austin, 1996.

Primary Examiner—Robert Raevis
Attorney, Agent, or Firm—Alston & Bird LLP

[57] ABSTRACT

An apparatus for compacting a material sample, such as paving material, including a cylindrical compaction mold and a mold support arranged to support one end of the mold. The mold support includes a turntable mounted for rotation about a rotational axis and a pair of mold-engaging members, such as rollers, extending from the turntable to engage the mold along its periphery and impart a gyratory motion to the mold as the turntable rotates. A mold retainer is also provided that includes a plurality of mold restraints spaced apart from one another about a central axis and arranged to engage the mold about the mold periphery at the end of the mold opposite the mold support. One of the mold restraints is attached to a movable latch that moves the mold restraint between an open position and a closed position. The open position locates the mold restraint out of engagement with the mold to allow the mold to slide into position inside the compactor apparatus. The closed position moves the mold restraint into contact with the mold and pushes the mold into a tilting position such that the axis of the mold intersects with the axis of the compression at the top of the mold. A compaction ram is mounted for axial movement into the mold along a predetermined axis of compression. As the ram applies compressive force, the turntable is rotated and the attached mold-engaging members impart a gyratory motion to the mold during compression.

26 Claims, 4 Drawing Sheets

GYRATORY COMPACTOR

FIELD OF THE INVENTION

The present invention relates to a materials testing apparatus, and more particularly an apparatus for compacting samples of paving material into standardized specimens for analysis.

BACKGROUND OF THE INVENTION

The physical properties of certain materials, such as paving materials, are measured by compacting loose samples of the material into test specimens under reproducible conditions using laboratory compaction machines. It is desirable to compact the test specimens under conditions that simulate actual use. For a paving material sample, this requires simulation of the kneading force applied to the paving material by the tires of passing vehicles. Simply applying a compressive force to the sample does not adequately simulate the kneading action of vehicular traffic. As a result, compaction machines that gyrate the sample during compression have been developed to simulate actual conditions of use.

An example of a gyratory compactor is illustrated in U.S. Pat. No. 5,323,655 to Eagan et al. and is herein incorporated by reference in its entirety. The gyratory compactor described therein includes a ram applying compressive force from one end of a cylindrical mold and gyrating the other end of the mold by rotating a base supporting the other end of the mold.

Notwithstanding the advances that have been made in the art of gyratory compactors, there is a need for smaller and less costly designs. Additionally, there is a need for a compactor having improved ergonomic design. For example, placement and removal of the mold containing the sample should be accomplished with minimal difficulty. Also, it would be advantageous to provide a compactor design that allows the user to quickly and easily change operating parameters, such as the angle of gyration. Further, there is a need in the art for a gyratory compactor that provides a constant angle of gyration during the compaction procedure with minimal deviation therefrom.

SUMMARY OF THE INVENTION

The compactor apparatus of the present invention provides an ergonomic and efficient design and offers improved consistency of operating parameters. The present invention allows the user to slide the cylindrical compaction mold into the compaction chamber without the necessity of lifting the mold. In addition, the present invention provides a frame design that reduces frame deflection that could undesirably affect the angle of gyration. The compactor apparatus of the present invention also includes an integral specimen removal ram. Further, the angle of gyration of the compactor apparatus is changed by simply replacing a single component of the apparatus.

The compactor apparatus of the present invention includes a cylindrical compaction mold having a central longitudinal mold axis. Preferably, the compaction mold has open opposite ends and is oriented in a generally vertical direction. The mold includes upper and lower peripheral flanges. The mold also includes compaction pucks within the cylindrical mold at either end.

The compactor apparatus further includes a compaction chamber adapted to receive the mold for compaction. The compaction chamber has an access door movable between a closed position preventing access to the mold within the chamber and an open position allowing placement or removal of the mold from the compaction chamber. A mold support and mold retainer are located within the compaction chamber.

The mold support is arranged for supporting one end of the compaction mold and includes a mold gyrator for imparting gyratory movement to one end of the compaction mold while the opposite end is held in place. The mold gyrator includes a turntable mounted for rotation about a rotational axis and a pair of mold-engaging members, such as rollers, extending from the turntable for engaging the compaction mold along its periphery during rotation of the turntable. The rollers are positioned in spaced apart relation from one another and arranged to allow for unobstructed sliding of the compaction mold into the compaction chamber. Movement of the rollers along the periphery of the mold imparts a gyratory movement to the mold during rotation of the turntable. The apparatus further includes a drive operatively connected to the turntable for imparting rotation thereto about a rotational axis.

The mold retainer includes a plurality of mold restraints spaced apart from one another about a central axis and arranged so as to engage the compaction mold at spaced locations about the mold periphery. The mold retainer engages the end of the mold opposite from the end supported by the mold support. A movable latch mounting one of the mold restraints is provided to allow movement between an open latch position and a closed position. The open position locates the mold restraint connected to the movable latch out of engagement with the compaction mold to allow for unobstructed movement of the mold into position in the compaction chamber and between the mold support and the mold retainer. The closed position locates the mold restraint in opposing cooperating relation with the other mold restraints to retain the mold in a desired position during compaction. The movable latch is positioned so as to tilt the mold axis a predetermined angle with respect to the axis of compression as the latch moves the mold restraint from the open position to the closed position. Preferably, the movable latch is mounted for movement in a plane perpendicular to the axis of compression for translationally moving the mold restraint toward and away from the axis of compression.

A material compaction ram is also included in the apparatus. The ram is mounted for axial movement into the compaction mold along a predetermined axis of compression to exert a compressive force upon the material contained within the mold. The axis of compression of the compaction ram is coincident with the central axis of the mold restraints and the rotational axis of the turntable. The rollers carried by the turntable are positioned to maintain an offset between said central longitudinal axis of the mold at the end of the mold engaging the rollers and the axis of compression. Thus, after the mold is tilted and the end of the mold opposite the rollers is held stationary, the rollers impart a gyratory movement to the end of the mold engaging the rollers as the turntable rotates. Preferably, the compaction ram is located centrally of the turntable and is mounted for movement into the mold from the lower end thereof. Preferably, the ram includes a bearing assembly carried by the ram that engages the lower compaction puck within the mold to reduce friction between the ram and the puck during gyration of the mold. In one embodiment, the apparatus further comprises a hub adjacent to the ram and the turntable. At least one shaft bearing and at least one rotational bearing assembly are carried by the hub. The shaft bearing is mounting the ram for axial movement and the rotational bearing assembly is rotatably mounting the turntable.

In one embodiment, the compactor apparatus includes a laterally extending mold support shelf positioned coplanar with the turntable and arranged to slidingly receive the compaction mold from the turntable. The mold support shelf is located outside of the compaction chamber. In a further embodiment, the support shelf carries a specimen removal ram mounted for upward axial movement along a vertical axis for removing a compacted specimen from a mold positioned on the support shelf. Preferably, a clutch assembly operatively connects the specimen removal ram to the drive for selectively powering the specimen removal ram using the same drive that rotates the turntable. The mold support shelf is carried by the frame and positioned for receiving and supporting a lower end of the compaction mold with the longitudinal mold axis oriented vertically.

The apparatus is carried by a frame. Preferably, the frame comprises three upright frame members located symmetrically and equidistantly about the compressive axis of the ram, in order to minimize changes in frame deflection and resulting mold angle variation during gyration.

BRIEF DESCRIPTION OF THE DRAWINGS

Some of the features and advantages of the invention having been described, others will become apparent from the detailed description which follows, and in the accompanying drawings, in which—

DESCRIPTION OF THE ILLUSTRATED EMBODIMENTS

The present invention will be described more fully hereinafter with reference to the accompanying drawings in which a preferred embodiment of the invention is shown. This invention may, however, be embodied in different forms and should not be construed as limited to the embodiments set forth herein; rather these embodiments are provided so that this disclosure will be thorough and complete and will fully convey the scope of the invention to those skilled in the art.

Figures 1, 2, 3:
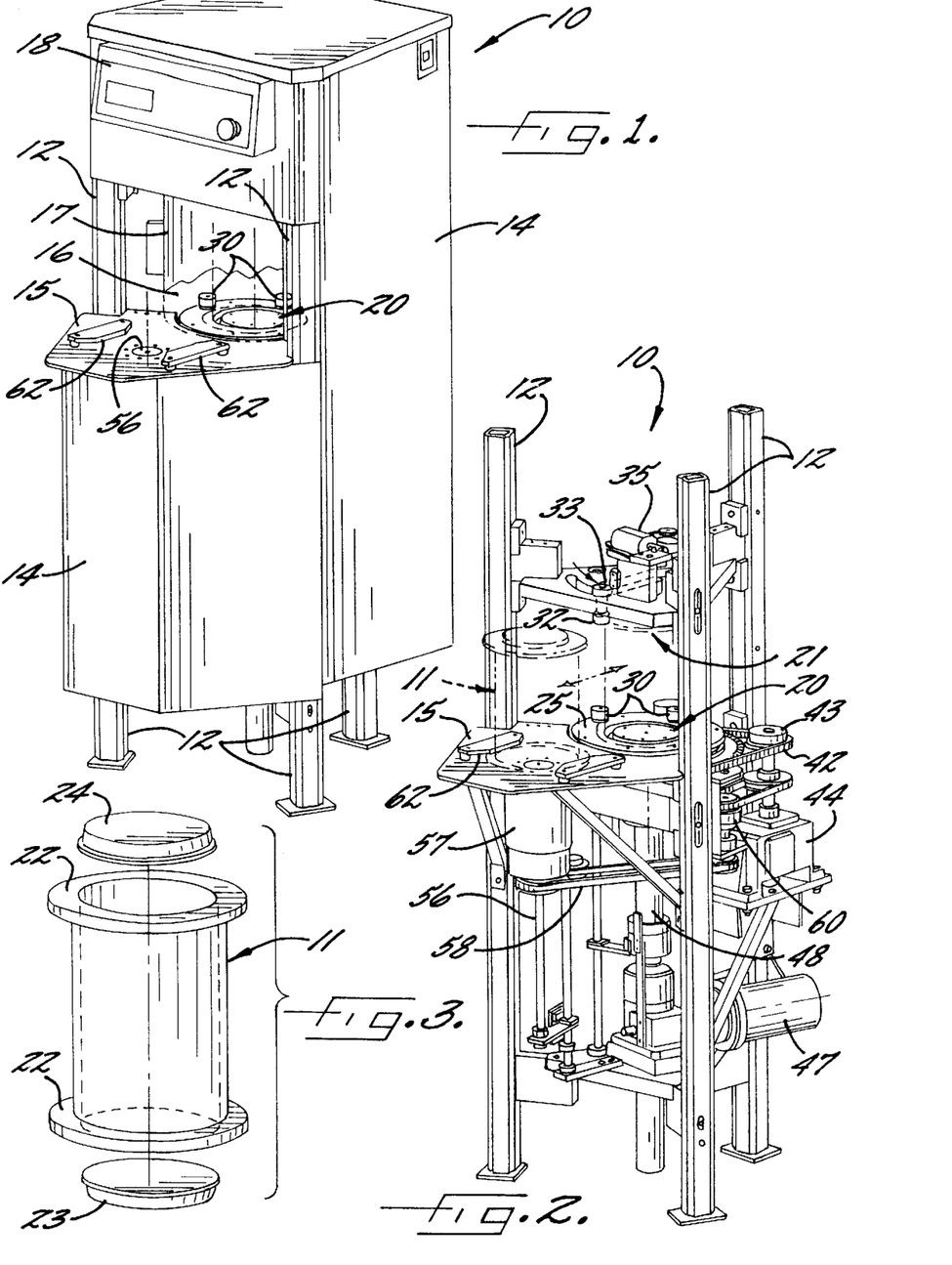
FIG. 1 is a front perspective view of a compactor apparatus in accordance with the present invention.
FIG. 2 is a front perspective view similar to FIG. 1, but with the exterior panels removed to reveal the interior components of the apparatus.
FIG. 3 is an exploded perspective view showing the mold used with the compactor apparatus.

Referring to FIG. 1, the compactor apparatus, indicated generally by the reference character 10, is designed for preparing test specimens of a sample of material, such as a sample of loose bituminous paving mixture, by means of gyratory shear compaction. The sample of material is placed in a cylindrical mold 11 (shown in FIG. 3) and the sample of material is compacted within the mold to form a cylindrical test specimen. As seen in FIG. 1, the compactor apparatus 10 includes upright frame members 12 surrounded by panels 14 which enclose the operative moving components of the apparatus. A laterally extending mold support shelf 15 is provided at the front of the apparatus 10 for receiving a cylindrical mold 11 with its axis oriented generally vertically. Behind the support shelf 15 is a compaction chamber 16 adapted to receive the mold 11 for compaction. A sliding door 17 is provided for enclosing the compaction chamber 16 during the compaction cycle of the apparatus 10. A control panel 18 on the front of the apparatus includes suitable controls, such as a keypad and a display for controlling operation of the apparatus 10.

Located within the compaction chamber 16 is a lateral mold support, generally indicated by the reference character 20, which is adapted for supporting the lower end of the cylindrical mold 11. The surface of the mold support 20 is coplanar with the surface of the mold support shelf 15 to allow the user to slide the mold 11 from the mold support shelf into the compaction chamber 16 without the necessity of lifting the mold. A mold retainer assembly, generally indicated at 21, is located within the compaction chamber 16 above the mold support 20 and is adapted for engaging and retaining the mold 11 at its upper end during the compaction cycle.

Figures 4, 5, 6:
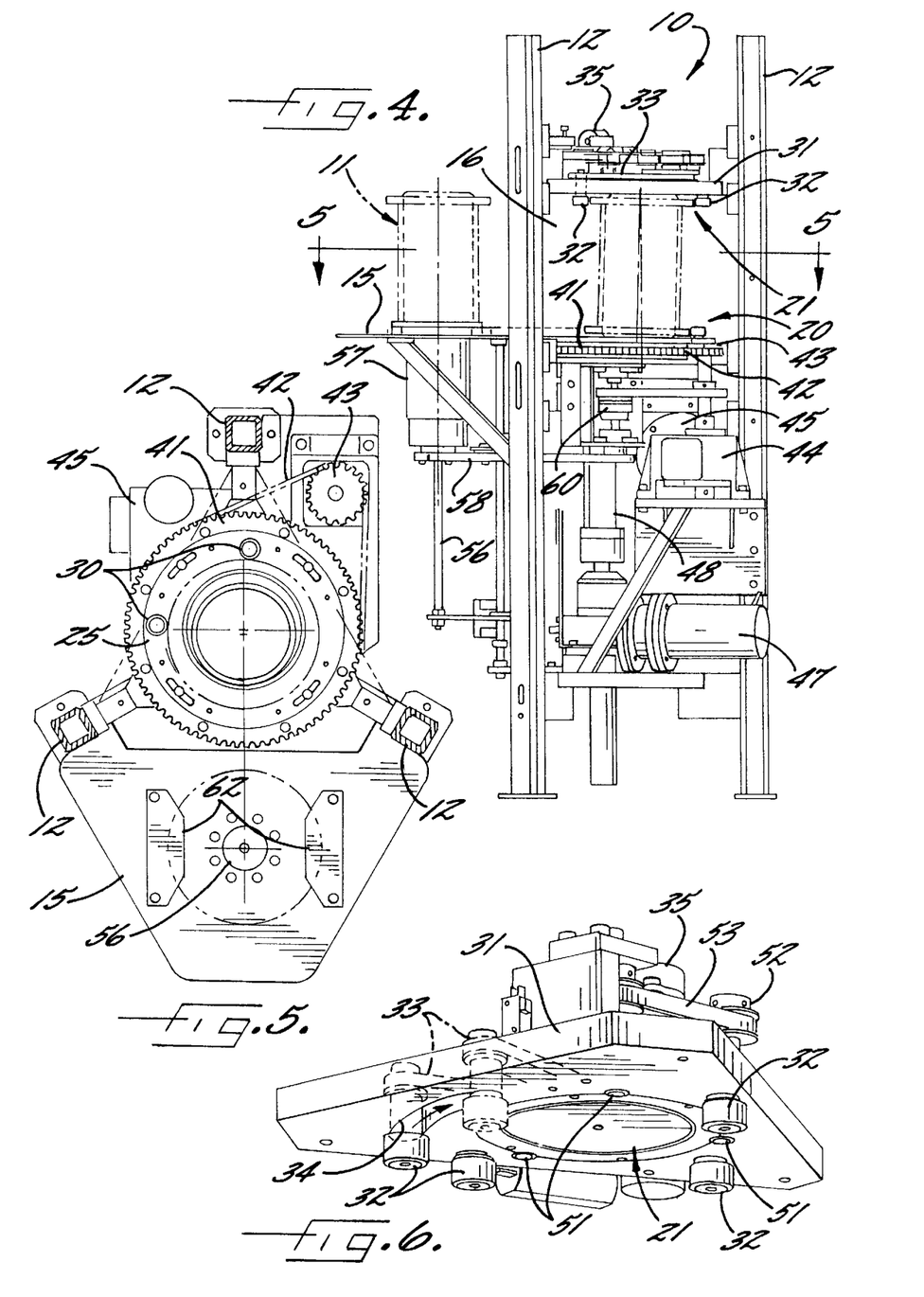
FIG. 4 is a side elevational view of the apparatus.
FIG. 5 is a cross sectional view through a portion of the apparatus taken substantially along the line 5—5 of FIG. 4.
FIG. 6 is a perspective view showing the mold retainer assembly.

As best seen in FIGS. 2 and 4, the mold 11 is positioned initially on the mold support shelf 15 with its longitudinal axis oriented vertically, i.e. perpendicular to the laterally extending support shelf surface. The mold 11 is cylindrical in shape and has open opposite ends. Upper and lower flanges 22 extend radially outwardly from the cylindrical mold 11 at the upper and lower ends thereof. Positioned within the mold 11 at its lower end is a lower compaction puck 23 (shown in FIG. 3) having an outside diameter corresponding to the inside diameter of the cylindrical mold with sufficient clearance to allow the puck 23 to move axially within the mold. The side walls of the compaction puck are preferably tapered to accommodate tilting of the mold 11 as explained more fully below. The material to be compacted, e.g. loose bituminous paving mix, is then placed in the mold 11 and the top of the mold is closed by an upper compaction puck 24. Like compaction puck 23, puck 24 is of a diameter corresponding to the inside diameter of the mold 11 so that the puck can move axially within the mold, and the lateral edges of the puck are preferably tapered to accommodate slight tilting of the mold during gyration of the material sample.

Once filled with material to be compacted, the mold 11 is moved into the compaction chamber 16 by sliding the mold across the surface of the mold support shelf 15 and onto the mold support 20. The mold support 20 comprises an annular turntable 25 which is mounted for rotation about a vertical axis of rotation by a bearing assembly 26. Located concentrically within the annular turntable 25 is a compression ram 28 which is movable axially along a vertical axis of compression for pushing the lower compaction puck 23 upwardly into the mold 11 to compact the material sample. The axis of compression of the compaction ram 28 and the rotational axis of the turntable 25 are coincident. The compression ram 28 is guided by shaft bearings 27. The bearing assembly 26 for the turntable 25 and the shaft bearings 27 for the ram 28 are carried by the same hub 64. Having both sets of bearings attached to a single component allows easier alignment of the turntable 25 rotation axis and the ram 28 compression axis during assembly of the apparatus 10. Having the ram 28 apply compressive force from the bottom reduces the overall height of the apparatus 10.

A ball bearing assembly 66 is attached to the end of the compression ram 28. The bearing assembly 66 is the interface between the compaction puck 23 and the compression ram 28. The bearing assembly 66 bears the compressive force from the ram 28 and moves in a circular path about the rotation axis as the mold gyrates. The bearing assembly 66 minimizes the horizontal load transmitted to the compression ram 28 by minimizing friction between the compaction puck 23 and the compression ram 28.

The annular turntable 25 has a pair of mold-engaging members in the form of freely rotatable rollers 30 mounted on its upper surface. As shown, the rollers 30 are secured to the upper face of turntable 25 and extend upwardly therefrom for engaging the lower flange 22 of mold 11. The rollers 30 are angularly spaced from one another a distance less than 180°. Thus, the rollers 30 engage the mold 11 on one side thereof while providing an unobstructed path allowing for sliding movement of the mold onto the turntable 25. The rollers 30 are positioned to offset the center of the bottom of the mold 11 from the rotational axis of the turntable 25 by a predetermined distance. When the annular turntable 25 is rotated, the rollers 30 act as cam followers, and the turntable 25 and rollers 30 collectively function as a mold gyrator to impart gyratory motion to the lower end of the mold 11 during the compaction cycle.

The upper end of the mold 11 is held by the mold retainer assembly 21 during the compaction cycle. The mold retainer assembly 21 includes a base plate 31 and a plurality of mold restraints 32 which are secured to the undersurface of the base plate at spaced locations about the central axis. In the embodiment shown, the mold restraints 32 are in the form of freely rotatable rollers which are positioned and arranged to engage the upper flange 22 of mold 11, although non-rotatable elements such as pins or the like could be employed. In the specific embodiment shown, the mold restraints 32 are four in number and they are equally spaced 90° from each other about the central axis. It should be evident that a different number of mold restraints 32 and a different arrangement could be suitably employed. For example, three mold restraints 32 could be used arranged 120° from one another, or two restraints, one fixed and one movable, could be used. In the embodiment shown, three of the mold restraints 32 are mounted directly to the base plate 31 and are thus in a fixed position. The fourth mold restraint 32 is mounted to a movable latch arm 33 which is pivotally mounted for movement in a plane parallel to the face of the base plate 31. An arcuate slot 34 allows the latch arm 33 to move the movable mold restraint 32 between an inoperative retracted position and an operative engaged position where the movable mold restraint is located in cooperating opposing relation with the fixedly mounted mold restraints for engaging the upper mold flange 22. Thus, the movably mounted mold restraint 32 forms a movable latch. In the operative closed position, the four mold restraints 32 engage the mold 11 at equally spaced locations about its periphery to thus restrain the upper end of the mold from lateral movement. When the latch is in the retracted inoperative position, the mold restraint 32 is moved out of the way to allow for sliding movement of the mold 11 into and out of position on the mold support 20. A latch arm actuator 35 located above the base plate 31 is arranged for moving the latch arm 33 between the inoperative retracted position and the operative closed position.

Figure 7:
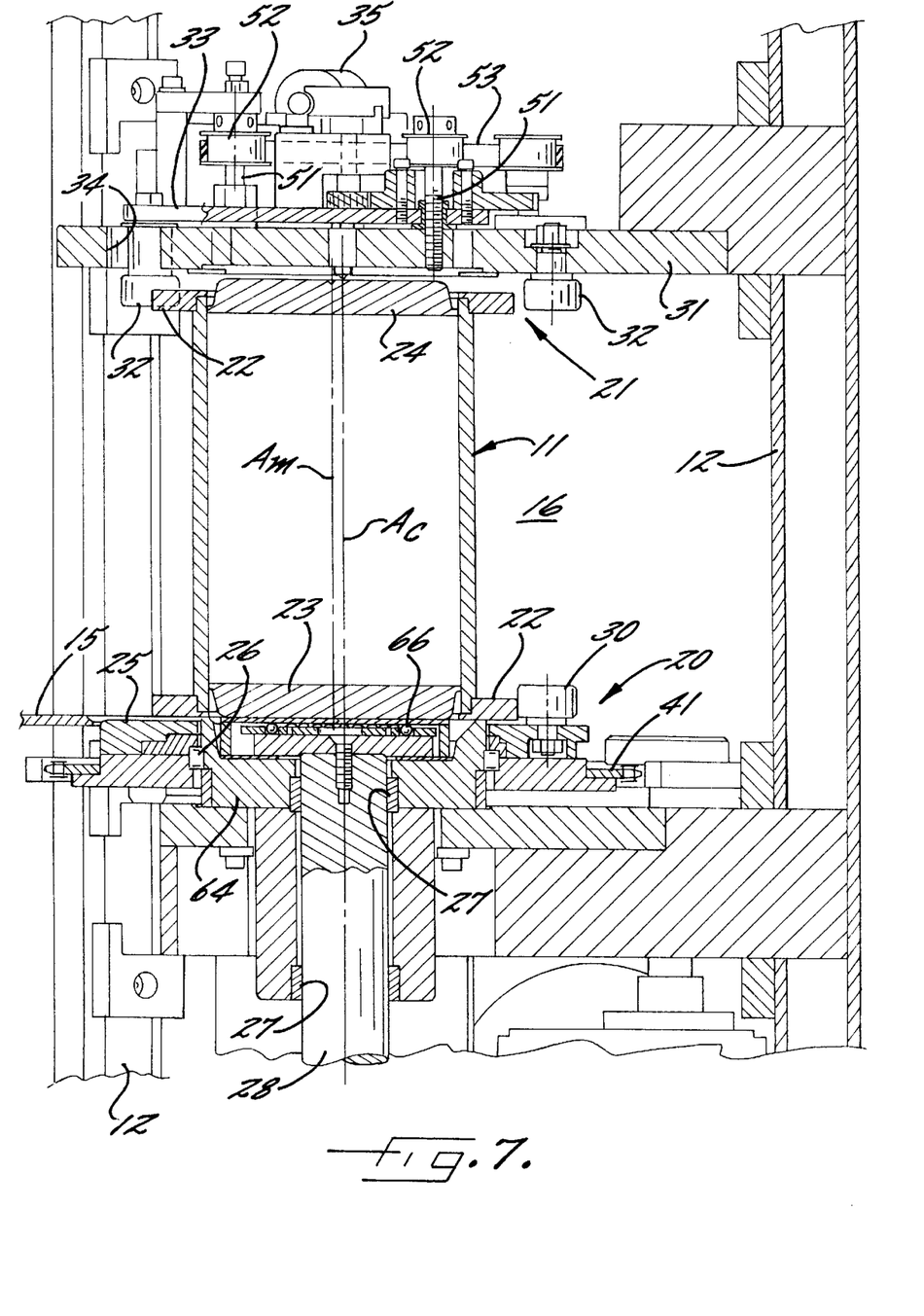
FIG. 7 is a side cross sectional view showing the mold positioned in the compaction chamber of the compactor apparatus prior to compaction.
Figure 8:
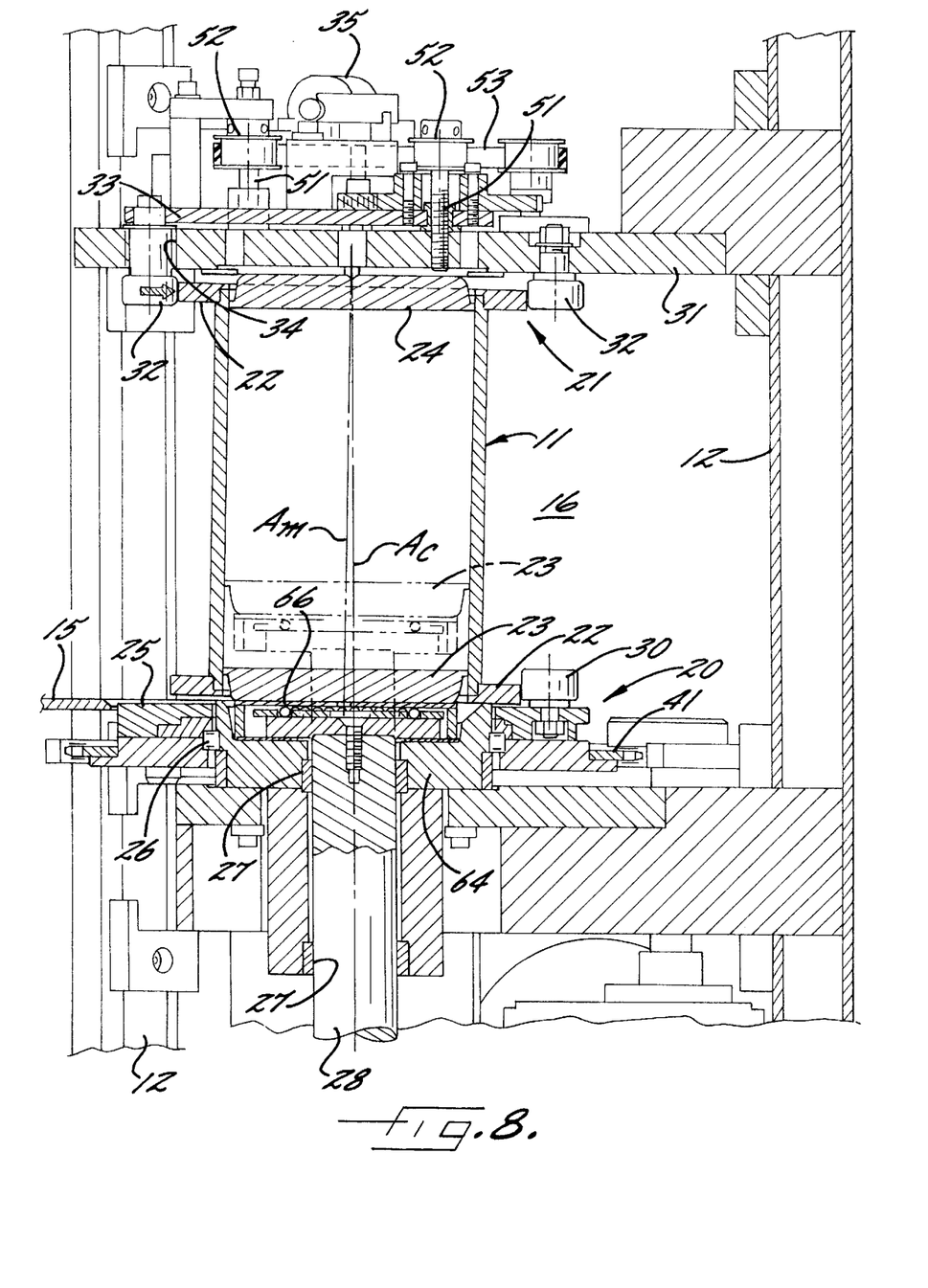
FIG. 8 is a side cross sectional view similar to FIG. 7, but showing how the mold is positioned during compaction.

Referring to FIG. 7, it will be seen that when the mold 11 is initially positioned in the compaction chamber, the lower end of the mold 11 is supported by the turntable 25 and the longitudinal axis of the mold is vertical. When the mold 11 is moved into a position so that the lower mold flange 22 seats against the two rollers 30, the mold axis Am is laterally offset but parallel to the axis of compression Ac of the ram 28. When the latch is moved to the closed position as shown in FIG. 8, the movable mold restraint 32 bears against the upper mold flange 22 and pushes the mold 11 until the mold flange seats against the fixedly mounted mold restraints. As a result, the mold 11 is tilted until the mold axis Am and the compressive axis Ac intersect at a point adjacent the upper end of the mold. The mold 11 is now tilted a predetermined and accurately controlled fixed angle. By way of nonlimiting example, a common mold angle used in the industry is 1.25°. However, the specific amount of mold tilt can be selected as desired by altering the geometry and arrangement of the rollers 30 on the angular turntable 25. If desired, the apparatus can be provided with a set of interchangeable turntables 25, each engineered for imparting a specific angle of mold tilt. In each case, the spacing of the rollers from one another and from the axis of rotation of the turntable 25 will establish a predetermined offset distance when the mold 11 is vertical and a predetermined angle when the mold is tilted.

With the mold 11 now having been placed in the compaction chamber 16 and with a specific angle of tilt imparted to the mold, the compaction cycle can be initiated. During the compaction cycle, the annular turntable 25 is rotated about its axis while the mold 11 is restrained from rotation. Since the axis of rotation of the turntable 25 is offset from the central longitudinal axis of the mold 11 at the bottom end of the mold engaging the rollers 30, the rollers force the bottom of the mold away from their rotational path as the turntable rotates. With the mold axis held stationary at its upper end, the lower end of the mold 11 is gyrated so that the mold axis gyrates about the longitudinal compressive axis of the ram 28. During this gyratory movement, the ram 28 is driven upwardly, as illustrated by the phantom lines in FIG. 8, to move the lower compaction puck 24 upwardly and to thus compress the material within the mold 11.

As shown in FIGS. 2, 4 and 5, the turntable 25 is rotated by a underlying turntable sprocket 41 which is driven by a drive chain 42 and drive sprocket 43. The drive sprocket 43 is mounted to a shaft extending from a transmission 44 which, in turn, is powered by a drive motor 45. The compression ram 28 is driven by a drive motor 47 and an associated jack screw 48.

The three upright frame members 12 are located symmetrically and equidistantly about the compressive axis of the ram. Because of the high forces exerted on the mold during compaction, the frame deflects horizontally and vertically due to the forces on the mold 11. The horizontal component of deflection varies as the mold 11 is gyrated, i.e., the horizontal force sweeps out a circle centered on the machine axis of rotation. Any significant deflection of the frame resulting from this horizontal force changes the mold angle. The rotationally symmetrical arrangement of frame components provides a stiff frame in which the mold angle will not vary due to frame deflection during gyration.

When the compaction cycle is completed, it is desirable to remove the tilt from the mold 11 and return it to an orientation with the longitudinal axis extending vertically prior to removing the mold from the compaction chamber 16. The tilt removal or leveling of the mold 11 is achieved by a series of leveling screws 51 which can be selectively driven downwardly from the base plate 31 to bear against the upper compaction puck 24 and to thus push the mold down and back to the vertical seated position shown in FIG. 7. The leveling screws 51 are threadably engaged with the base plate 31. Pulleys 52 provided at the upper end of the screws are driven by a drive belt 53 to thereby rotate the screws 51 and cause them to be extended from the base plate 31 or to be retracted.

After leveling of the mold 11, the sliding door 17 may be opened and the mold may be moved back onto the mold support shelf 15. To facilitate extraction of the compacted sample from the mold 11, the lower mold flange 22 is positioned beneath and between the pair of mold flange retainers 62 which restrain the mold from upward movement while a specimen extraction ram 56 pushes axially upwardly on the lower compaction puck 23 to push the sample upwardly and free it from the mold. The extraction ram 56 is moved axially by a jack screw 57 which, in turn, is rotated by a drive belt 58. A clutch assembly 60 selectively powers the drive belt 58 from the output shaft of transmission 44. Thus, the same drive motor 44 which is used for rotating the turntable can be used selectively for driving the extraction ram.

Many modifications and other embodiments of the invention will come to mind to one skilled in the art to which this invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed is:

1. A compactor apparatus comprising:
    a cylindrical compaction mold having a central longitudinal mold axis;
    a mold support arranged for supporting one end of said mold;
    a mold retainer positioned opposite said mold support for retaining the opposite end of said mold;
    a material compaction ram mounted for axial movement into said mold along a predetermined axis of compression to exert a compressive force upon material within said mold;
    said mold retainer including a plurality of mold restraints spaced apart from one another about a central axis and arranged so as to engage the mold at spaced locations about the mold periphery; and
    a movable latch mounting one of said mold restraints for movement between an open position and a closed position, the open position locating said one mold restraint out of engagement with the mold to allow for unobstructed movement of the mold into position between said mold support and said mold retainer, and said closed position locating said one mold restraint in opposing cooperating relation with the other of said mold restraints to retain the mold in a desired position during compaction by said compaction ram.

2. A compactor apparatus according to claim 1, wherein said movable latch is mounted for movement in a plane perpendicular to said axis of compression for translationally moving said one mold restraint toward and away from said axis of compression.

3. A compactor apparatus according to claim 1, further comprising a frame, wherein said frame comprises a plurality of upright frame members located symmetrically about said axis of compression of said ram.

4. A compactor apparatus comprising:
    a cylindrical compaction mold having a central longitudinal mold axis oriented generally vertically;
    a laterally extending mold support arranged for supporting a lower end of said mold, said mold support including a turntable mounted for rotation about a rotational axis and a pair of mold-engaging members extending from said turntable for engaging said mold along its periphery during rotation of the turntable;
    a mold retainer positioned above said mold support for retaining the upper end of said mold, said mold retainer including a plurality of mold restraints spaced apart from one another about a central axis and arranged so as to engage the mold adjacent its upper end at spaced locations about the mold periphery;
    a movable latch mounting one of said mold restraints for movement between an open position out of engagement with the mold to allow for unobstructed movement of the mold onto said turntable and a closed position engaging said mold; and
    a material compaction ram mounted for axial movement into said mold along a predetermined axis of compression to exert a compressive force upon material within said mold.

5. A compactor apparatus according to claim 4, wherein said movable latch is so positioned and arranged as to tilt the mold axis a predetermined angle with respect to said axis of compression as the latch moves said one mold restraint from said open position out of engagement with the mold to said closed position engaging said mold.

6. A compactor apparatus according to claim 4, wherein said rotational axis of said turntable is coincident with the axis of compression of said compaction ram such that movement of said mold-engaging members along the periphery of said mold imparts a gyratory motion to the mold during rotation of said turntable.

7. A compactor apparatus according to claim 4, wherein said compaction ram is located centrally of said turntable and is mounted for movement into said mold from said lower end thereof.

8. A compactor apparatus according to claim 7, wherein the axis of compression of said compaction ram is coincident with said central axis of said mold restraints.

9. A compactor apparatus according to claim 4, wherein said mold includes upper and lower peripheral flanges, said mold-engaging members engaging said lower peripheral flange, and said mold restraints engaging said upper peripheral flange.

10. A compactor apparatus according to claim 4, additionally including a laterally extending mold support shelf positioned coplanar with said turntable and arranged for slidingly receiving said mold from said turntable.

11. A compactor apparatus according to claim 10, including a compaction chamber adapted to receive said mold for compaction, said mold support and said mold retainer being located within said compaction chamber, and said mold support shelf being located outside of said compaction chamber, and including an access door movable between a closed position preventing access to the mold within said compaction chamber and an open position allowing for placement or removal of the mold in said compaction chamber.

12. A compactor apparatus comprising:
    a cylindrical compaction mold having a central longitudinal mold axis and open opposite ends; a frame;
    a laterally extending mold support shelf carried by said frame and positioned for receiving and supporting a lower end of said mold with the longitudinal mold axis oriented vertically;
    a turntable mounted adjacent said mold support shelf, said turntable being positioned coplanar with said shelf for slidingly receiving said mold from said support shelf;

a drive operatively connected to said turntable for imparting rotation thereto about a rotational axis;

a pair of mold-engaging members carried by said turntable and extending therefrom for engaging said mold adjacent its lower end, said mold-engaging members being positioned in spaced apart relation from one another and arranged to allow for unobstructed sliding of the mold from said support shelf onto said turntable and to impart a gyratory motion to the mold during rotation of the turntable;

a mold retainer positioned above said turntable, said mold retainer including a plurality of mold restraints spaced apart from one another about a central axis and arranged so as to engage said mold adjacent its upper end at spaced locations about the mold periphery;

a movable latch mounting one of said mold restraints for movement between an open position out of engagement with the mold to allow for unobstructed sliding of the mold from said support shelf onto said turntable and a closed position engaging said mold; and a material compaction ram mounted for axial movement into said mold along a predetermined axis of compression to exert a compressive force upon material within said mold.

13. A compactor apparatus according to claim 12, wherein said frame comprises a plurality of upright frame members located symmetrically about said axis of compression of said ram.

14. A compactor apparatus according to claim 13, wherein said compaction ram is mounted centrally of said turntable and is insertable axially upwardly into said mold.

15. A compactor apparatus according to claim 13, wherein said plurality of mold restraints on said upper mold support are located at equally spaced locations about said central axis, said central axis being coincident with said compressive axis.

16. A compactor apparatus according to claim 13, including a specimen removal ram carried by said support shelf and mounted for upward axial movement along a vertical axis for removing a compacted specimen from a mold positioned on said support shelf.

17. A compactor apparatus according to claim 16, including a clutch assembly operatively connecting said specimen removal ram with said drive for selectively powering said specimen removal ram from said drive.

18. A compactor apparatus comprising:

a cylindrical compaction mold having open opposite ends a central longitudinal mold axis oriented vertically;

a turntable positioned for supporting said lower end of said mold;

a drive operatively connected to said turntable for imparting rotation thereto about a rotational axis;

a pair of mold-engaging members carried by said turntable and extending therefrom for engaging said mold adjacent its lower end, said mold-engaging members being positioned in spaced apart relation from one another and arranged to allow for unobstructed sliding of the mold onto said turntable and to impart a gyratory motion to the mold during rotation of the turntable;

a mold retainer positioned above said turntable, said mold retainer including a plurality of mold restraints arranged at spaced locations about a central axis and engaging said mold adjacent its upper end;

a movable latch mounting one of said mold restraints for movement between an open position out of engagement with the mold to allow for unobstructed sliding of the mold onto said turntable and a closed position engaging said mold; and a material compaction ram mounted for axial movement into said mold along a predetermined axis of compression to exert a compressive force upon material within said mold.

19. A compactor apparatus comprising:

a cylindrical compaction mold having a central longitudinal mold axis and open opposite ends;

a laterally extending mold support shelf positioned for receiving and supporting a lower end of said mold with the longitudinal mold axis oriented vertically;

a compaction chamber located adjacent said mold support shelf and adapted for receiving said mold for compaction;

a mold support located within said compaction chamber and positioned for supporting said lower end of said mold, said mold support being located coplanar with said mold support shelf for slidingly receiving said mold from said support shelf;

a mold retainer located within said compaction chamber opposite said mold support for retaining the upper end of said mold;

said mold retainer including mold restraint means movable between an inoperative open position allowing for unobstructed sliding movement of the mold from said support shelf and onto said mold support with the mold axis oriented vertically, and to an operative closed position in which the mold is restrained at its upper end and the mold axis is tilted a predetermined angle from said vertical orientation;

a mold gyrator associated with said mold support for imparting gyratory movement to said mold about said predetermined mold angle; and a material compaction ram mounted for axial movement into said mold along a predetermined axis of compression to exert a compressive force upon material within said mold during said gyratory movement of the mold.

20. A compactor apparatus comprising:

a cylindrical compaction mold having a central longitudinal mold axis;

a mold support arranged for supporting one end of said mold;

a mold retainer positioned opposite said mold support for retaining the opposite end of said mold;

a material compaction ram mounted for axial movement into said mold along a predetermined axis of compression to exert a compressive force upon material within said mold;

said mold retainer including a plurality of mold restraints spaced apart from one another about a central axis and arranged so as to engage the mold at spaced locations about the mold periphery; and a movable latch mounting one of said mold restraints for movement between an open position and a closed position, the open position locating said one mold restraint out of engagement with the mold to allow for unobstructed movement of the mold into position between said mold support and said mold retainer, and said closed position locating said one mold restraint in opposing cooperating relation with the other of said mold restraints to retain the mold in a desired position during compaction by said compaction ram, wherein said movable latch is so positioned and arranged as to tilt the mold axis a predetermined angle with respect to said axis of compression as the latch moves said one mold restraint from said open position out of engagement with the mold to said closed position engaging said mold.

21. A compactor apparatus comprising:

a cylindrical compaction mold having a central longitudinal mold axis;

a mold support arranged for supporting one end of said mold;

a mold retainer positioned opposite said mold support for retaining the opposite end of said mold;

a material compaction ram mounted for axial movement into said mold along a predetermined axis of compression to exert a compressive force upon material within said mold;

said mold retainer including a plurality of mold restraints spaced apart from one another about a central axis and arranged so as to engage the mold at spaced locations about the mold periphery;

said mold support including a mold gyrator for imparting gyratory movement to said one end of said mold while said opposite end of the mold is held by said mold retainer; and a movable latch mounting one of said mold restraints for movement between an open position and a closed position, the open position locating said one mold restraint out of engagement with the mold to allow for unobstructed movement of the mold into position between said mold support and said mold retainer, and said closed position locating said one mold restraint in opposing cooperating relation with the other of said mold restraints to retain the mold in a desired position during compaction by said compaction ram.

22. A compactor apparatus according to claim 21, wherein said mold gyrator includes a turntable mounted for rotation about a rotational axis and a plurality of mold-engaging members extending from said turntable for engaging said mold along its periphery during rotation of the turntable.

23. A compactor apparatus according to claim 22, wherein the axis of compression of said compaction ram is coincident with both said central axis of said mold restraints and said rotational axis of said turntable.

24. A compactor apparatus according to claim 23, wherein said mold-engaging members are positioned to maintain an offset between said central longitudinal axis of said mold and said axis of compression, said mold-engaging members imparting a gyratory movement to said end of said mold as said mold-engaging members revolve about said rotational axis of said turntable.

25. A compactor apparatus according to claim 22, further comprising a compaction puck within said mold and a bearing assembly carried by said ram and engaging said puck to reduce friction between said ram and said puck during gyratory movement of said mold.

26. A compactor apparatus according to claim 22, further comprising a hub adjacent to said ram and said turntable, at least one shaft bearing carried by said hub and mounting said ram for axial movement and at least one rotational bearing assembly carried by said hub and rotatably mounting said turntable.

* * * * *

UNITED STATES PATENT AND TRADEMARK OFFICE
CERTIFICATE OF CORRECTION

PATENT NO. : 5,939,642
DATED : August 17, 1999
INVENTOR(S) : King et al.

It is certified that error appears in the above-identified patent and that said Letters Patent is hereby corrected as shown below:

Column 9, lines 29, 32 and 37, "claim 13", each occurrence, should read --claim 12--.

Signed and Sealed this

Twenty-second Day of August, 2000

Attest:

Q. TODD DICKINSON

*Attesting Officer*        *Director of Patents and Trademarks*